US006420629B1

(12) United States Patent
Xue et al.

(10) Patent No.: US 6,420,629 B1
(45) **Date of Patent: *Jul. 16, 2002**

(54) PROCESS OF INCREASING PLANT GROWTH AND YIELD AND MODIFYING CELLULOSE PRODUCTION IN PLANTS

(75) Inventors: Bao Guo Xue; Craig Hunter Newton; Benjamin Charles Sherbrooke Sutton; John Robert Gawley, all of Vancouver; David Dunham Ellis, Tsawwassen, all of (CA)

(73) Assignee: B.C. Research Inc., Vancouver (CA)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/707,860

(22) Filed: Sep. 9, 1996

(51) Int. Cl.[7] ........................... A01H 1/00; A01H 5/00; A01H 5/10; C12N 15/00; C12N 15/52

(52) U.S. Cl. ....................... 800/284; 800/288; 800/290; 800/298; 435/468; 435/320.1; 435/536; 536/23.2

(58) Field of Search ................................ 800/278, 288, 800/284, 290, 298, 315, 316, 317, 317.3; 435/320.1, 468; 536/23.2

(56) References Cited

U.S. PATENT DOCUMENTS

| | | | | |
|---|---|---|---|---|
| 5,079,162 A | | 1/1992 | Ben-Bassat et al. | |
| 5,122,466 A | | 6/1992 | Stomp et al. | |
| 5,268,274 A | | 12/1993 | Ben-Bassat et al. | |
| 5,382,656 A | | 1/1995 | Benziman et al. | |
| 5,436,394 A | | 7/1995 | Willmitzer et al. | |
| 5,492,820 A | | 2/1996 | Sonnewald et al. | |
| 5,498,830 A | | 3/1996 | Barry et al. | |
| 5,498,831 A | | 3/1996 | Burgess et al. | |
| 5,597,718 A | | 1/1997 | John et al. | |
| 5,608,149 A | | 3/1997 | Barry et al. | |
| 5,646,023 A | | 7/1997 | Secor et al. | |
| 5,705,375 A | | 1/1998 | Van Ooyen et al. | |
| 5,714,365 A | | 2/1998 | Van Assche et al. | |
| 5,716,837 A | | 2/1998 | Barry et al. | |
| 5,723,757 A | | 3/1998 | Rocha-Sosa et al. | |
| 5,723,764 A | * | 3/1998 | Nichols et al. | 800/205 |
| 5,750,869 A | | 5/1998 | Shewmaker | |
| 5,750,876 A | | 5/1998 | Barry et al. | |
| 5,759,828 A | | 6/1998 | Tal et al. | |
| 5,767,365 A | | 6/1998 | Sonnewald | |
| 5,773,693 A | | 6/1998 | Burgers et al. | |
| 5,773,699 A | | 6/1998 | Kerr et al. | |
| 5,792,630 A | | 8/1998 | Tonouchi et al. | |
| 5,792,920 A | | 8/1998 | Bridges et al. | |
| 5,792,921 A | | 8/1998 | Londesborough | |
| 5,824,790 A | | 10/1998 | Keeling et al. | |
| 5,824,798 A | | 10/1998 | Tallberg et al. | |
| 5,856,467 A | | 1/1999 | Hofvander et al. | |
| 5,859,333 A | | 1/1999 | Keeling et al. | |
| 5,866,790 A | * | 2/1999 | Hesse et al. | 800/205 |
| 5,990,390 A | * | 11/1999 | Lundquist et al. | 800/302 |

FOREIGN PATENT DOCUMENTS

| | | | | |
|---|---|---|---|---|
| EP | 485044 | * | 5/1992 | C12N/15/55 |
| EP | 0 628 636 A1 | | 12/1994 | |
| WO | 92/18631 | * | 10/1992 | C12N/15/54 |
| WO | WO 96/21737 | | 7/1996 | |
| WO | WO 98/00549 | | 1/1998 | |
| WO | 98/03637 | * | 1/1998 | C12N/9/10 |

OTHER PUBLICATIONS

Haigler, C.H. et al. Proceedings of the National Academy of Sciences 93:12082–12085, Oct. 1996.*

Zrenner, R. et al. Planta 190:247–252, 1993.*

Matzke, M. et al. Plant Physiology 107:679–685, 1995.*

Finnegan, J. et al. Bio/Tehnology 12:883–888, Sep. 1994.*

Kleczkowski, L.A., "Glucose Activation and Metabolism through UDP–Glucose Pyrophosphorylatse in Plants," *Phytochemistry*, vol. 37, No. 6, 1994, pp. 1507–1515, XP002061889.

Martin, Thomas et al., "Expression of an *Arabidopsis*sucrose synthase gene indicates a role in metabolization of sucrose both during phloem loading and in sink organs," *The Plant Journal*, vol. 4, No. 2, 1993, pp. 367–377, XP002061421.

Foyer, C.H. et al., "Modifications in Carbon Assimilation, Carbon Partitioning and Total Biomass as a Result of Over–Expression of Sucrose Phosphates Synthase in Transgenic Tomato Plants," *Plant Physilolgy*, vol. 105, No. 1, May 1994, p. 23 XP002002230.

Delmer, Deborah P. et al., "Cellulose Biosythesis," *The Plant Cell*, vol. 7, 1995, pp. 987–1000, XP002061423.

Xue, Bao et al., "Altering Carbon Allocation to Increase Cellulose Biosynthesis and Plant Production," *Plant Physiology*, supplement, vol. 114, No. 3, Jul. 1997, p. 300, XP002061450.

Brown, R. Malcolm et al., "Cellulose Biosynthesis in Higher Plants," *Trends in Plant Science*, vol. 1, No. 5, May 1996, pp. 149–156.

Amor, Yehudit et al., "A Membrane–Associated Form of Sucrose Synthase and its Potential Role in Synthesis of Cellulose and Callose in Plants," *Proc. Natl. Acad. Sci. USA*, vol. 92, pp. 9353–9357, Sep. 1995, Plant Biology.

Kudlicka, Krystyna et al., "β–Glucan Synthesis in the Cotton Fiber[1], " *Plant Physiol.*(1995) 107: 111–123.

(List continued on next page.)

*Primary Examiner*—Mary E. Mosher

(57) ABSTRACT

A process of increasing plant growth and yield comprises introducing into the plant a DNA sequence encoding a product which modifies, in the plant, the level of cellulose precursors.

18 Claims, 6 Drawing Sheets

OTHER PUBLICATIONS

Nakano, Kenichi et al., "UDP–Glucose Pyrophosphorylase from Potato Tuber: Purification and Characterization[1], " *J. Biochem.*, vol. 106, No. 3, 1989, pp. 528–532.

Slay, Raymond M. et al., "Characterization of the UDP–glucose: (1,3)–β–glucan (callose) synthase from plasma membranes of celery: polypeptide profiles and photolabeling patterns of enriched fractions suggest callose synthase complexes from various sources share a common structure," *Plants Science*, 86 (1992) 125–136.

Sonnewald, Uwe et al., "Molecular Approaches to Skin-Source Interactions," *Plant Physiol.*(1992) 99, 1267–1270.

Sonnewald, Uwe et al., "Increased potato tuber size resulting from apoplastic expression of a yeast invertase," *Nature Biotechnology*, vol. 15, Aug. 1997, pp. 794–797.

Spychalla, James P. et al., "Cloning, Antisense RNA Inhibition and the Coordinated Expression of UDP–Glucose Pyrophosphorylase with Starch Biosynthetic Genes in Potato Tubers," *J. Plant Physiol.*, vol. 144, pp. 444–453 (1994).

Valla, Svein et al., "Cloning of a gene involved in cellulose biosynthesis in *Acetobacter xylinum*: Complementation of cellulose–negative mutants by the UDPG pyrophosphorylase structure gene," *Mol Gen Genet*(1989) 217: 26–30.

Strak, David. M. et al. "Regulation of the Amount of Starch in Plant Tissues by ADP Glucose Pyrophosphorylase," *Science*, vol. 258, Oct. 1992, pp. 287–292.

* cited by examiner

```
                                      V  I  K  P  L  K  K  A  V  L  P  V  A  G  L  G  T  R  F  L  P  A  T  K  C   25
A. xylinum           tcatgcatcttgaggtaaatattaGTGattaagccccttaaaaaagccgtattgccggttgccggccttggaacacgctttctgcccgccaccaagtgcg 100
pAX6 binary vector                           cggtaccATGGTCAAGCCCCTTAAAAAAGCCGTATTGCCGGTTGCCGGCCTTGGAACACGCTTTCTGCCCGCCACCAAGTGCG 100
                                      M  V  K  P  L  K  K  A  V  L  P  V  A  G  L  G  T  R  F  L  P  A  T  K  C   33

                     V  P  K  E  M  L  T  V  V  D  R  P  L  I  Q  Y  A  I  D  E  A  R  E  A  G  I  E  E  F  C  L  V  S  S 59
A. xylinum           tgcccaaggaaatgctgaccgttgttgaccgtccgctgatccagtatgcgattgacgaggcacgcgaagccgggatcgaggaattctgcctcgtttccag 200
pAX6                 TGCCCAAGGAAATGCTGACCGTTGTTGACCGTCCGCTGATCCAGTATGCGATTGACGAGGCACGCGAAGCCGGGGTCGAGGAATTCTGCCTCGTTTCCAG 200
                     V  P  K  E  M  L  T  V  V  D  R  P  L  I  Q  Y  A  I  D  E  A  R  E  A  G  V  E  E  F  C  L  V  S  S 67

                     R  G  K  D  S  L  I  D  Y  F  D  I  S  Y  E  L  E  D  T  L  K  A  R  K  K  T  S  A  L  K  A  L  E  92
A. xylinum           ccggggcaaggattccctgatcgattatttcgacatttcctacgaactcgaagacacgctgaaggcccgcaagaagacatcggcactgaaggccctggaa 300
pAX6                 CCGGGGCAAGGATTCCCTGATCGATTATTtCGACATTTCATACGAACTCGAAGACACGCTGAAGGCCCGCAAGAAGACATCGGCACTGAAGGCCCTGGAA 300
                     R  G  K  D  S  L  I  D  Y  F  D  I  S  Y  E  L  E  D  T  L  K  A  R  K  K  T  S  A  L  K  A  L  E

                     A  T  R  V  I  P  G  T  M  L  S
A. xylinum           gcaacccgcgtcatcccgggcaccatgctgtccg
pAX6                 GCAACCCGCGTCATCCCGGGCACCATGTTGTCCG
                     A  T  R  V  I  P  G  T  M  L  S
```

FIG. 2

SEQUENCE LISTING

<160> NUMBER OF SEQ ID NOS: 11

<210> SEQ ID NO 1
<211> LENGTH: 46
<212> TYPE: DNA
<213> ORGANISM: Artificial Sequence
<220> FEATURE:
<223> OTHER INFORMATION: Description of Artificial Sequence:5'- Primer
<221> NAME/KEY: CDS
<222> LOCATION: (16)..(45)

<400> SEQUENCE: 1
taggatccgt cgacc atg gtc aag ccc ctt aaa aaa gcc gta ttg c 46
Met Val Lys Pro Leu Lys Lys Ala Val Leu
1 5 10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence:5'- Primer

<400> SEQUENCE: 2

Met Val Lys Pro Leu Lys Lys Ala Val Leu
1 5 10

<210> SEQ ID NO 3
<211> LENGTH: 52
<212> TYPE: DNA
<213> ORGANISM: Acetobacter xylinum
<220> FEATURE:
<221> NAME/KEY: CDS
<222> LOCATION: (16)..(48)

<400> SEQUENCE: 3
ttgaggtaaa tatta gtg att aag ccc ctt aaa aaa gcc gta ttg ccg gttg 52
Val Ile Lys Pro Leu Lys Lys Ala Val Leu Pro
1 5 10

<210> SEQ ID NO 4
<211> LENGTH: 11
<212> TYPE: PRT
<213> ORGANISM: Acetobacter xylinum

<400> SEQUENCE: 4

Val Ile Lys Pro Leu Lys Lys Ala Val Leu Pro
1 5 10

<210> SEQ ID NO 5
<211> LENGTH: 48
<212> TYPE: DNA
<213> ORGANISM: Acetobacter xylinum -continued

```
<400> SEQUENCE: 5

ggtgccggaa gatcacttgt acttcgtcag gaattcacgc acgccggg              48


<210> SEQ ID NO 6
<211> LENGTH: 6
<212> TYPE: PRT
<213> ORGANISM: Acetobacter xylinum

<400> SEQUENCE: 6

Ser Asn Val Cys Ala Pro
  1               5


<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence:3'-Primer

<400> SEQUENCE: 7

ggtgcctcta gatcacttgt acttcgtcag gacttcacgc acgccggg              48


<210> SEQ ID NO 8
<211> LENGTH: 334
<212> TYPE: DNA
<213> ORGANISM: Acetobacter xylinum
<220> FEATURE:
<221> NAME/KEY: CDS
<222> LOCATION: (25)..(333)

<400> SEQUENCE: 8

tcatgcatct tgaggtaaat atta gtg att aag ccc ctt aaa aaa gcc gta       51
                           Val Ile Lys Pro Leu Lys Lys Ala Val
                             1               5

ttg ccg gtt gcc ggc ctt gga aca cgc ttt ctg ccc gcc acc aag tgc      99
Leu Pro Val Ala Gly Leu Gly Thr Arg Phe Leu Pro Ala Thr Lys Cys
 10                  15                  20                  25

gtg ccc aag gaa atg ctg acc gtt gtt gac cgt ccg ctg atc cag tat     147
Val Pro Lys Glu Met Leu Thr Val Val Asp Arg Pro Leu Ile Gln Tyr
                 30                  35                  40

gcg att gac gag gca cgc gaa gcc ggg atc gag gaa ttc tgc ctc gtt     195
Ala Ile Asp Glu Ala Arg Glu Ala Gly Ile Glu Glu Phe Cys Leu Val
             45                  50                  55

tcc agc cgg ggc aag gat tcc ctg atc gat tat ttc gac att tcc tac     243
Ser Ser Arg Gly Lys Asp Ser Leu Ile Asp Tyr Phe Asp Ile Ser Tyr
         60                  65                  70

gaa ctc gaa gac acg ctg aag gcc cgc aag aag aca tcg gca ctg aag     291
Glu Leu Glu Asp Thr Leu Lys Ala Arg Lys Lys Thr Ser Ala Leu Lys
     75                  80                  85

gcc ctg gaa gca acc cgc gtc atc ccg ggc acc atg ctg tcc g           334
Ala Leu Glu Ala Thr Arg Val Ile Pro Gly Thr Met Leu Ser
 90                  95                 100


<210> SEQ ID NO 9
<211> LENGTH: 103
<212> TYPE: PRT
<213> ORGANISM: Acetobacter xylinum

<400> SEQUENCE: 9

Val Ile Lys Pro Leu Lys Lys Ala Val Leu Pro Val Ala Gly Leu Gly
  1               5                  10                  15

Thr Arg Phe Leu Pro Ala Thr Lys Cys Val Pro Lys Glu Met Leu Thr
             20                  25                  30
```

-continued

```
Val Val Asp Arg Pro Leu Ile Gln Tyr Ala Ile Asp Glu Ala Arg Glu
        35                  40                  45

Ala Gly Ile Glu Glu Phe Cys Leu Val Ser Ser Arg Gly Lys Asp Ser
    50                  55                  60

Leu Ile Asp Tyr Phe Asp Ile Ser Tyr Glu Leu Glu Asp Thr Leu Lys
 65                 70                  75                  80

Ala Arg Lys Lys Thr Ser Ala Leu Lys Ala Leu Glu Ala Thr Arg Val
                85                  90                  95

Ile Pro Gly Thr Met Leu Ser
            100


<210> SEQ ID NO 10
<211> LENGTH: 317
<212> TYPE: DNA
<213> ORGANISM: Acetobacter xylinum
<220> FEATURE:
<221> NAME/KEY: CDS
<222> LOCATION: (8)..(316)

<400> SEQUENCE: 10

cggtacc atg gtc aag ccc ctt aaa aaa gcc gta ttg ccg gtt gcc ggc       49
        Met Val Lys Pro Leu Lys Lys Ala Val Leu Pro Val Ala Gly
          1               5                  10

ctt gga aca cgc ttt ctg ccc gcc acc aag tgc gtg ccc aag gaa atg       97
Leu Gly Thr Arg Phe Leu Pro Ala Thr Lys Cys Val Pro Lys Glu Met
 15                 20                  25                  30

ctg acc gtt gtt gac cgt ccg ctg atc cag tat gcg att gac gag gca      145
Leu Thr Val Val Asp Arg Pro Leu Ile Gln Tyr Ala Ile Asp Glu Ala
                35                  40                  45

cgc gaa gcc ggg gtc gag gaa ttc tgc ctc gtt tcc agc cgg ggc aag      193
Arg Glu Ala Gly Val Glu Glu Phe Cys Leu Val Ser Ser Arg Gly Lys
            50                  55                  60

gat tcc ctg atc gat tat ttc gac att tca tac gaa ctc gaa gac acg      241
Asp Ser Leu Ile Asp Tyr Phe Asp Ile Ser Tyr Glu Leu Glu Asp Thr
        65                  70                  75

ctg aag gcc cgc aag aag aca tcg gca ctg aag gcc ctg gaa gca acc      289
Leu Lys Ala Arg Lys Lys Thr Ser Ala Leu Lys Ala Leu Glu Ala Thr
    80                  85                  90

cgc gtc atc ccg ggc acc atg ttg tcc g                                317
Arg Val Ile Pro Gly Thr Met Leu Ser
 95                 100


<210> SEQ ID NO 11
<211> LENGTH: 103
<212> TYPE: PRT
<213> ORGANISM: Acetobacter xylinum

<400> SEQUENCE: 11

Met Val Lys Pro Leu Lys Lys Ala Val Leu Pro Val Ala Gly Leu Gly
  1               5                  10                  15

Thr Arg Phe Leu Pro Ala Thr Lys Cys Val Pro Lys Glu Met Leu Thr
            20                  25                  30

Val Val Asp Arg Pro Leu Ile Gln Tyr Ala Ile Asp Glu Ala Arg Glu
        35                  40                  45

Ala Gly Val Glu Glu Phe Cys Leu Val Ser Ser Arg Gly Lys Asp Ser
    50                  55                  60

Leu Ile Asp Tyr Phe Asp Ile Ser Tyr Glu Leu Glu Asp Thr Leu Lys
 65                 70                  75                  80

Ala Arg Lys Lys Thr Ser Ala Leu Lys Ala Leu Glu Ala Thr Arg Val
```

-continued

```
                85                  90                  95

Ile Pro Gly Thr Met Leu Ser
           100
```

PROCESS OF INCREASING PLANT GROWTH AND YIELD AND MODIFYING CELLULOSE PRODUCTION IN PLANTS

FIELD OF THE INVENTION

The present invention relates to processes of enhancing plant growth and productivity and more specifically, to the field of carbon re-allocation in plants.

BACKGROUND OF THE INVENTION

Increasing harvestable plant yield is a major goal of all plant breeding efforts. In fiber producing crops, the economic value of this yield is directly related to the amount, location, and length of the cellulose fibers. It has been suggested that cellulose content and fiber yield is limited by the amount of substrate, or sugars, produced during photosynthesis. However, numerous studies provide evidence that although crucial for plant growth and survival, the availability of carbohydrates derived from photosynthesis are not major limiting factors in cellulose synthesis. Thus there exists a substantial opportunity to increase fiber yield by creating a sink for this existing photosynthate in cells high in cellulose. Sucrose, the major form of translocatable carbohydrate produced during photosynthesis in the plant, is translocated to sink tissue where it is converted to other compounds such as starch or cellulose.

Despite the fact that the amount of photosynthates in the plant are not a primary limitation in cellulose content, the rate of photosynthesis plays a large role in the overall growth of a plant. Further, one element in the control of photosynthesis in the plant is the feedback-inhibition of photosynthesis by photosynthetic products, such as starch, sucrose and hexose sugars. Goldschmidt and Huber (1992)[1] tested the effect of girdling the leaves of crop plants and demonstrated that the build up of starch and other products of photosynthesis actually inhibited the rate of photosynthesis. These findings, and others (Sonnewald & Willmitzer 1992)[2], indicate the photosynthetic rate, and ultimately plant growth, may be directly correlated with the rate that photosynthates are drawn away from the leaf, or the rate of biosynthetic degradation in the leaves. The degradation of photosynthates occurs primarily in cells/tissues that are actively growing (meristematic or young tissues) or in tissues where photosynthates are utilized for storage or structural components (sink tissues). Therefore altering the rate that carbohydrates are translocated to these sink tissues (altering carbon allocation) would not only increase overall plant growth (remove inhibitors of photosynthesis), but also increase the amount of storage (starch) or structural components (cellulose).

A striking example of the benefits of altering carbon allocation has been demonstrated in potato. By increasing the synthesis and accumulation of ADP-glucose in the tuber, starch synthesis increased which significantly increased dry matter content. In fact, this resulted in a 25% increase in tuber yield. The increase in ADP-glucose in the tuber was accomplished by genetically engineering the potato with a bacterial ADP-glucose pyrophosphorylase gene controlled by a tuber specific promoter (Shewmaker and Stalker 1992) [3].

Much like ADP-glucose is a precursor to starch synthesis, the nucleotide sugar UDP-Glucose, (UDPG), is a high energy substrate for cellulose biosynthesis in both bacteria and higher plants (Delmer 1987[4]. Delmer et al. 1995[5]). Several bacterial genes which encode the enzyme UDP-glucose pyrophosphorylase (UDPG-PPase), responsible for the synthesis of UDPG, have been isolated (Ross et al. 1991[6]). An existing patent by Betlach (1987[7]) claims increased synthesis of xanthan and other polysaccharides in bacteria by insertion of a UDPG-PPase gene from *Xanthamonas campestris*. However, the claims in this patent are limited to increasing polysaccharide biosynthesis in prokaryotic organisms.

It is an object of the present invention to obviate or mitigate the above disadvantages.

SUMMARY OF THE INVENTION

The present invention provides a process of increasing plant growth and yield which comprises introducing into a plant a DNA sequence encoding a product which modifies, in the plant, the level of cellulose precursors. This product of the present invention includes, but is not limited to, ribonucleic acid ("RNA") molecules, enzymes related to cellulose biosynthesis and proteins which regulate the expression of these enzymes.

It has been found that the process of the present invention leads to the reallocation by simple diffusion of carbohydrates such as glucose from photosynthetic cells, such as the leaf cells, to other cells within the plant. This translocation removes the inhibition on photosynthesis imposed by excess photosynthate accumulation in these photosynthetic cells thereby allowing the plant to produce more simple sugars by continued photosynthesis. In other words, as photosynthesis continues in an uninhibited fashion, more simple sugars are produced than would have otherwise have been possible. These simple sugars are building blocks for plant growth via the production of polymers such as starch and cellulose.

Further, the present invention provides a process of modifying the production of cellulose in a plant which comprises introducing into said plant a DNA sequence encoding a product which modifies, in the plant, the level of cellulose substrates. As above, the product includes, but is not limited to, ribonucleic acid ("RNA") molecules, enzymes related to cellulose biosynthesis and proteins which regulate the expression of these enzymes.

The subject invention also provides a plant having increased growth and yield and/or modified cellulose producing activity as a result of introducing into said plant or parent of said plant a DNA sequence coding for a product which modifies the level of cellulose precursors in the plant.

Another aspect of the present invention provides for a DNA expression vector comprising a DNA sequence encoding a product which modifies, in a host, the level of cellulose precursors, said sequence being operably linked to an expression affecting DNA sequence and flanked by translational start and stop sequences.

The present invention also provides a genetically modified seed comprising a DNA sequence, said sequence encoding a product capable of increasing growth and yield and/or modifying the level of cellulose precursors in the plant resulting from said seed.

There are two primary features of the process of the present invention. Firstly, in all plants regardless of whether they are fiber-producing (trees, hemp, cotton etc..) or not, what is achieved are plants having faster rates of growth and increased yield by non-specifically re-allocating carbon within the plant away from photosynthetic cells. This allows photosynthesis to continue uninhibited to produce more simple "construction" sugars thereby enhancing the efficiency of the plant growth rate and increasing growth yield. Secondly, in fiber-producing plants, the expression of the DNA sequence introduced into the plant may be targeted to specific individual cell types within the plant to increase predictably cellulose deposition in a cell specific manner. In forest trees, this is expected to increase wood production and fiber yield, especially when the gene is linked to a promoter which expresses only in wood forming tissues. Increased fiber yield can also be expected in other non-forestry fiber producing plants, such as hemp and sisal. In addition to targeting wood forming tissues, increased cellulose production can be obtained in other parts of the plant such as the boles surrounding the seeds of cotton plants.

Specific applications for increased cellulose synthesis include numerous crops with diverse uses and growth habits. In forestry, wood production is influenced by a combination of physiological and biochemical processes governed by substantial genetic variation. This has lead to the theoretical consideration of limitations on increasing yield due to fundamental constraints on energy supply (Farnum 1983[8]). Despite such limitations, increases in tree growth of 50 to 300% are possible depending on the tree species and growing environment. Clearly, improving energy capture, conversion of radiant energy, and altering carbon allocation within the plant are promising areas for tree improvement. Increasing cellulose content by the processes outlined herein can achieve such gains.

BRIEF DESCRIPTION OF THE DRAWINGS

The present invention is described by way of the following non-limiting drawings in which:

FIG. 2 represents the nucleotide and amino acid sequences of Alxylinium and the cloned gene cassettes in the pBI series of binary vectors SEQ ID Nos. 8, 9,10 and 11);

PREFERRED EMBODIMENTS OF THE INVENTION

Figure 1:
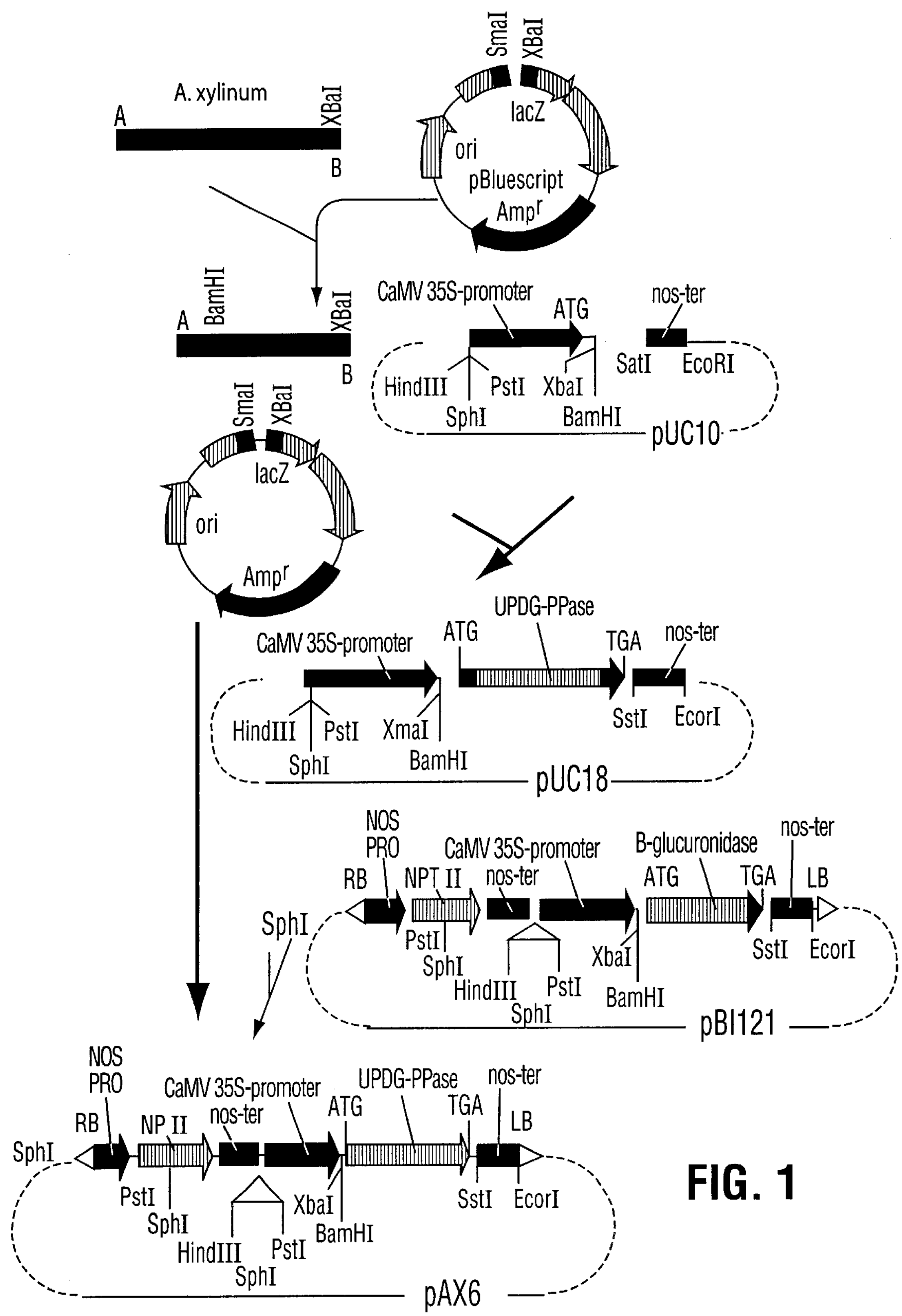
FIG. 1 illustrates schematically the formation gene cassette comprising the UDPG-PPase gene and CaMV promoter, the cloning vector pUC comprising the gene cassette and transformation vectors pBI121 and pAX6 comprising the gene cassette and preferential promoters.

The present invention affords the ability to increase plant growth rates and yield through the addition to the plants of DNA sequences encoding products which have a modifying role on the level of cellulose precursors. The result of the introduction and expression in the plant of this DNA sequence is the beneficial and optionally selective allocation of carbon within the plant.

In a preferred form of the invention described further hereinbelow, the DNA sequence may be selectively expressed in cells primarily responsible for cellulose synthesis. By creating a sink for these carbohydrates in cellulose producing cells, excess photosynthate can be diverted to these cells where the default pathway for their use would be conversion into cellulose, thereby increasing cellulose content in the plant. For example, in trees, as photosynthate such as sucrose and hexose sugars are removed from the leaves to the stem the inhibitory effect of these compounds on photosynthesis is removed. This has huge implications in forestry, because whether harvesting for lumber or fiber, the product is cellulose. The benefit of increased cellulose is not limited, however, to forestry, as there are numerous other fiber crops including sisal, cotton, and hemp.

In one embodiment of the present invention, the product encoded by the inserted DNA sequence is an enzyme such as a carbohydrate-modifying enzyme selected from the group consisting of uridine diphosphate-glucose pyrophosphorylase ("UDPG-PPase"), sucrose synthetase, cellulose synthase or any derivative thereof Sucrose synthetase is responsible for the synthesis of uridine diphosphate-glucose ("UDP-glucose") in plants. The present application is not limited to the specific enzymes disclosed herein as these are intended merely as a sampling of preferred enzymes. What is required for the enzymes to be useful herein is that they have the potential to affect, in some way, the level of cellulose precursors in the plant. These enzymes may originate from any organism including other plant species, bacteria or yeast.

Although bacterial enzymes are preferred for the reasons described below, it is to be understood that the DNA sequences encoding enzymes may originate from many other organisms. The key criteria in selecting a "preferred" enzyme is a relatively high Km value for the product as compared to the precursors or substrates thereby indicating a preference in the reaction toward the product.

UDP-PPase is the most preferred enzyme particularly when the DNA sequence encoding the enzyme originates from bacteria. The enzyme kinetics data ( UDPG-PPase has a relatively high Km value for UDPG as compared to the substrates UTP, glucose-1-phosphate and PPi), lack of signal sequences and the fact that, unlike the corresponding plant gene, the bacterial UDPG-PPase gene is not strongly inhibited by UDPG accumulation make the bacterial UDPG-PPase gene an excellent target gene to increase UDPG levels in plants. Additionally, bacterial genes are widely available and are less likely to lead to co-suppression of the native UDPG-PPase genes. Bacterial genes may be selected from many commonly available genera, but in a preferred form are selected from the genus Acetobacter, more specifically from the species including *Acetobacter xylinum* and from the genus Xanthomonas.

In an alternative embodiment, the DNA sequence introduced into the plant may encode regulatory, feedback or other proteins which affect cellulose biosynthesis in plants or any derivatives thereof These include lignin-modifying proteins and proteins which regulate lignin-modifying proteins.

In a further embodiment, the DNA sequence introduced into the plant encodes for an RNA molecule having regulatory properties. For example, these RNA molecules may effect enzyme synthesis, cellulose synthesis or may indirectly modify cellulose synthesis through an alteration in precursor or lignin synthesis.

Prior to the introduction of the DNA sequence into the plant cells as described further hereinbelow, the DNA sequence or gene of interest (terms "DNA sequence" and "gene" used hereinafter interchangeably) encoding for the product with cellulose modulatory effects is prepared into a DNA construct or vector. Initially, the gene of interest is extracted by known techniques from the source (for example, bacteria, yeast or other plant species.) or obtained from a depository such as ATCC. The general extraction procedure involves lysing the cells of the source and recovering the released DNA through extraction such as phenol/chloroform with a final precipitation in, for example, alcohol.

The gene or DNA sequence is then amplified by, for example, the polymerase chain reaction ("PCR") and subsequently cloned into the desired construct or vector. The amplification of the gene based on the PCR makes use of primers and inducing agents, sometimes referred to as enzyme catalysts. The PCR process is described in considerable detail in U.S. Pat. No. 4,800,159 and Canadian Patent No. 1,237,685 both to Cetus Corporation and in U.S. Pat. Nos. 4,965,188 and 4,682,202 all of which are incorporated herein by reference.

The term "primer" as used herein refers to an oligonucleotide, whether occurring naturally as in a purified restriction digest or produced synthetically, which is capable of acting as a point of initiation of DNA synthesis when placed under conditions in which synthesis of a primer extension product which is complementary to the nucleotide sequence is induced, i.e. in the presence of nucleotides and inducing agent and at a suitable pH and temperature. The primer is preferable single-stranded for maximum efficiency in amplication but may alternatively be double-stranded. If double-stranded, the primer is first treated to separate its strands before being used to prepare the extention products. Preferably, the primer is an oligodeoxyribonucleotide. The exact lengths of the primers may be different for each DNA sequence or "template" to be amplified. Generally, a balance must be struck with respect to primer size. It must be large enough to be usefully specific to the template, that is, it must be homologous to a large enough region of the template so that other extraneous DNA (not related to the DNA sequence) with some degree of homology to the primer is not amplified to a significant extent. On the other hand, the size of the primer should not be so large as to be unwieldy and prohibitive in terms of time and cost. This balance may be achieved for most of the DNA sequences contemplated within the scope of the present invention with primer of between 10–50 nucleotides in length. The determination of the appropriate lengths of primers, however, is well within the purview of a technician of average skill in this area. In addition, although the PCR is an efficient process for producing exponential quantities of a DNA product relative to the number of reaction steps involved, other known DNA amplification techniques may be used within the scope of the present invention.

Suitable constructs or vectors for transforming the plant host are well known in the art and include plasmids, cosmids, phage derivatives, phasmids and expression vectors. General vectors of interest may contain an origin of replication functional in one or more plant species, convenient restriction endonuclease digestion sites and selectable markers for the plant cell. Preferred transformation vectors vary depending on the particular host but include Bluescript vectors, pBI (Agrobacterium binary vectors) and pUC derived vectors. Other vectors useful for assessing MRNA and protein expression in plants include pMAL and pGEM vectors.

In order to achieve expression of the DNA sequence of interest in a plant host, it may be necessary to make modifications to the regulatory and/or controlling sequences of that DNA. Specifically, it may be necessary to link the gene of interest operably to an expression effecting DNA sequence, such as one or more promoters and to flank it with translational start and stop signals. In particular, the start codon may be changed and suitable plant promoter and terminator sequences added. Optionally, an improved translation consensus sequences may be provided. It is to be understood, however, that these modifications need not be made for each and every DNA sequence contemplated within the scope of the present invention. The question of making these technical modifications is well within the purview of a technician of average skill in this field.

A number of promoters may be ligated to the DNA sequence, the most efficient type of which varies between plant hosts. In a preferred form, the promoter expresses specifically in vascular plant cells or cellulose-producing cells within the plant. For example, in trees, xylem specific promoters including, but not limited to the 4-coumarate CoA ligase ("4CL") promoter from parsley are preferred in order to direct expression to wood-forming tissues. In tobacco plants, suitable promoters include the cauliflower mosaic virus ("CaMV") 35S promoter. In other plant species, 4CL and CaMv 35S among others may be used.

For consistency in terminology, the DNA sequence to be transformed having modifications to the regulatory and/or controlling sequences is referred to hereinafter as a "gene cassette" or "DNA sequence cassette". Transformation of this DNA sequence cassette into a plant host may be achieved by a number of established methods. Generally for most plants including tobacco, the widely practised Agrobacterium transformation method is appropriate. General techniques for transformation of plants can be found in Svab Z. P. Hajdukiewicz and P. Maliga. 1995. Generation of Transgenic Tobacco Plants by Agrobacterium Transformation. pp. 61–77. (eds. P. Maliga, D. F. Klessig, A. R. Cashmore, W. Gruissem and J. E. Varner) *Methods in Plant Molecular Biology,* Cold Spring Harbor Laboratory Press, New York and Horsch, R. B., J. E. Fry, N. L. Hoffman, D. Eichholtz, S. G. Rogers and R. T. Fraley. 1985. A Simple and General Method for Transferring Genes into Plants. *Science* 227:1229–1231 both of which are incorporated herein by reference. In a preferred form for trees, in particular coniferous species such as spruce, the particle gun bombardment method may be used in conjunction with embryonic cultures.

In the particle gun bombardment process, which is described in more detail in the incorporated reference: Ellis et al. 1993. Stable Transformation of Picea glauca by Particle Acceleration. *Bio/Technology. vol.* 11 pp. 84–89, embryonic cultures of the plant host are exposed, for short time, to a blast or bombardment of the DNA sequence or DNA sequence cassette to be transformed. Generally, this is achieved by inert gas (such as helium) propulsion of microparticles of gold coated with the DNA sequence to be transformed. Optionally, the DNA sequence may be fused to a marker gene, such as an antibiotic resistance gene to allow for subsequent selection of cultures for further regeneration. For example, the DNA sequence may be fused to a kanamycin resistance gene and the transformed cultures thereafter selected for plant regeneration on the basis of kanamycin resistance.

After transformation, the plant tissue is preferably placed on an antibiotic containing medium on which the transformed cells expressing a resistance gene are able to grow. Non-transformed cells are thereby retarded in their growth and/or die on the antibiotic. In this manner, once plants are regenerated either through the formation of shoots or the development of mature embryos and germination (as is the case with somatic embryogenesis), only plants capable of expressing the introduced genes (the DNA sequence of the present invention together with the antibiotic resistance gene) are produced.

The seeds (including artificial seeds derived from somatic embryos) and subsequent plants resulting from the transformation and regeneration process as described herein have increased rates of growth and increased yields as a result of the transformed DNA sequence which modifies the level of cellulose precursors in the plant. For example, if the transformed DNA sequence comprises the UDPG-PPase gene, glucose (a photosynthate) is converted in plant cells to UDP-glucose (a high energy substrate for celluose biosynthesis). As these plant cells then have a lesser concentration of glucose relative to photosynthetic cells, glucose translocates by simple diffusion to these cells. This carbon translocation reduces the inhibition of excess photosynthate on photosynthesis leading to more efficient photosynthesis and enhanced sugar production. In a preferred form, when the DNA sequence expression is targeted to vascular or cellulose-producing cells via specific promoters, not only is there carbon re-allocation as described above, but there is provided more UDP-glucose in these cells allowing for enhance cellulose production with the attendant advantages.

EXAMPLES

Summary

Transformation of tobacco with a construct for overexpression of an *Acetobacter xylinum* (Ax) UDPG-PPase gene has resulted in increased dry weight, solute content, and a-cellulose content in the transformants relative to non-transformed control plants. Antibody specific to the Ax UDPG-PPase gene has been generated in rabbits following injection of a fusion protein overproduced in *E. coli.* Using this antibody, detection of expressed UDPG-PPase in transgenic tobacco has been confirmed. The inserted gene cassette segregated based on kanamycin resistance in most of the $T_1$ population in a manner consistent with a single insertion site. Initial experiments with the transformation of two constructs, a 4CL-GUS and a 4CL-UDPG-PPase in spruce has yielded numerous putative transformed lines. These lines are currently undergoing GUS screening (4CL-GUS) and further kanamycin screening (both constructs).

Example 1

Preparation of DNA constructs

The original bacterium (*Acetobacter xylinum*) containing the gene UDP-glucose pyrophosphorylase (LDPG-PPase) was obtained from ATCC (23768). The UDPG-PPase gene was amplified by PCR and subsequently cloned. Design of the PCR primers included the following considerations:

Addition of restriction sites suitable for cloning into a variety of transformation vectors.

Mutation of the start codon from valine to methionine

Mutation of internal Eco RI site to remove it without change in amino acid sequence.

Addition of non-coding DNA fragment at the 5' end of the gene to enhance the efficiency of translation.

The resulting primer A at the 5' end is:

(MVKPLKKAVL) (SEQ ID NO:2)

taGGATCCgtcgaccATGGTCAAGccccttaaaaaagccgtattgc (SEQ ID NO:1)

and the original UDPG-PPase gene at 5' end is:

ttgaggtaaatattaGTGATTAAgccccttaaaaaagccgtattgccggttg→(SEQ ID NO:3)

VIKPLKKAVLP (SEQ ID NO:4)

The original UDPG-PPase gene at the 3' end is:

ggtgccggaagatcacttgtacttcgtcaggaattcacgcacgccggg (SEQ ID NO:5)

Stop code*SNVCAP (SEQ ID NO:6)

and the primer B at the 3' end is:

ggtgccTCTAGAtcACTTGTacttcgtcagGACTTCacgcacgccggg (SEQ ID NO:7)

Stop code*SN*VCAP (SEQ ID NO:6)

Amplification of the gene was successful and DNA sequencing confirmed that the amplified fragment was the UDPG-PPase gene. The amplified UDPG-PPase gene from *A. xylinum* is almost identical to the published sequences.

The complete DNA sequence has been analyzed to detect potential exon and intron splice sites. Several characters have been considered to find introns which could potentially cause splicing of the MRNA. These include no-random codons in the DNA sequence, preferential usage of certain codons, GC content, relative positions of purines and pyrimidines in the codons of known sequences, and exon value of regions between splice sites, as well as downstream and upstream of the end of the exon. Analysis showed that the potential of mRNA splicing in plant tissue was low.

The amplified UDPG-PPase sequence was cloned into a BlueScript vector and used for construction of the gene cassettes. The gene cassette was constructed by ligating the UDPG-PPase gene with a CaMV 35S promoter. A pUC based cloning vector containing the UDPG-PPase gene with suitable restriction sites for placing the "gene cassette" in a variety of transformation vectors containing xylem preferential and other promoters was made. FIG. I shows that gene cassettes and vectors.

Figure 3:
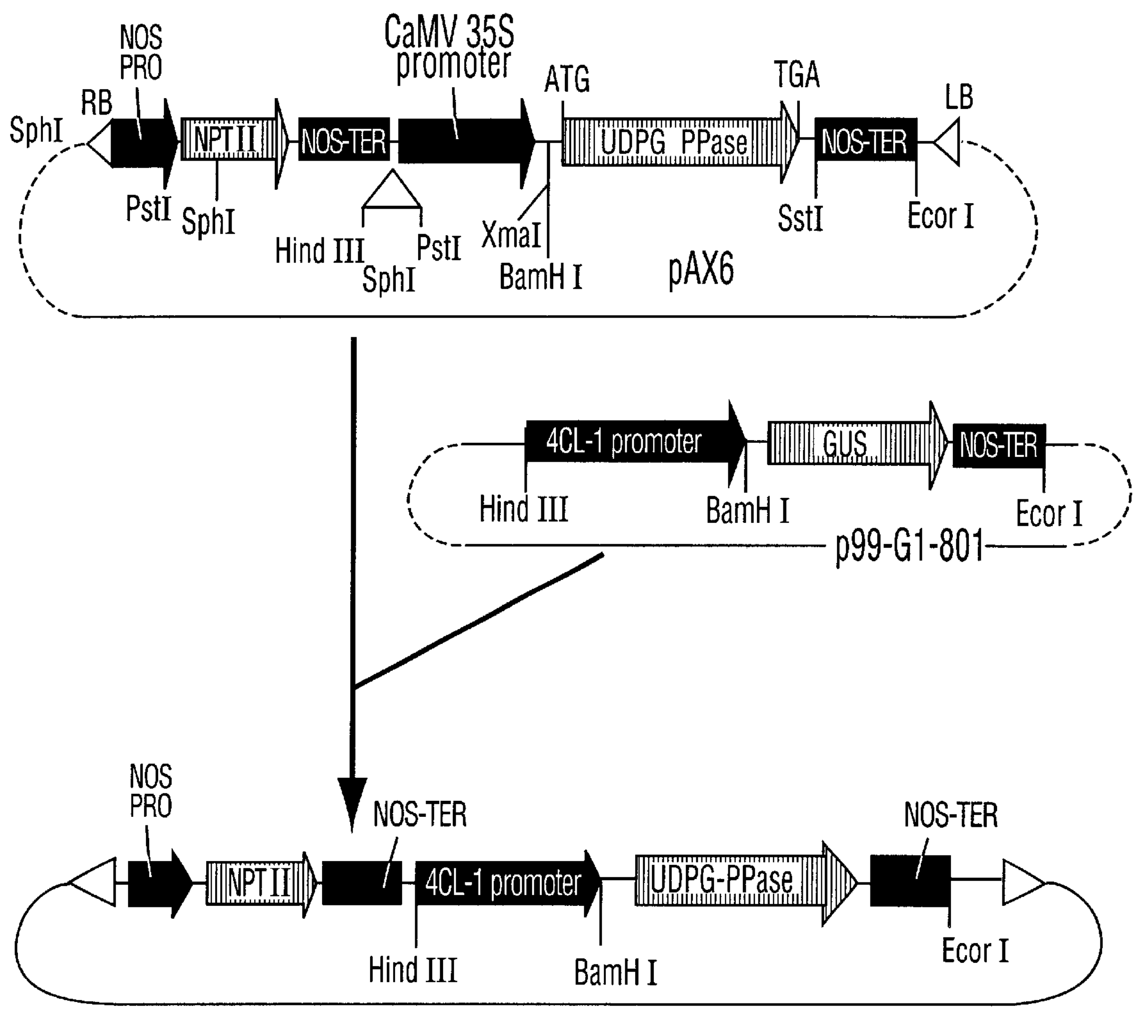
FIG. 3 illustrates schematically the formation of the xylem specific transformation vector with the UDPG-PPase gene.

Several vectors containing the UDPG-PPase gene from *Acetobacter xylinum* (Ax) have been derived from the gene cassette for different purposes, as follows:

For tobacco transformation:

pBIAx—Agrobacterium binary vector with the Ax gene linked to CAMV 35S promoter pBI4CLAx—A grobacterium binary vector with the Ax gene linked to a parsley 4CL promoter for xylem preferential expression For spruce transformation:

pBI4CLAX—pUC-derived vector, containing Ax linked to 4CL promoter p4CLGUS—pUC-derived vector containing GUS linked to a parsley 4CL promoter for assessment of xylem specificity of the promoter For assessing mRAVA and protein expression in transformants:

pMAL—protein expression vector in *E. coli,* for antibody production.

pGem—MRNA transcriptional vector, for in situ hybridization.

pBI based binary vectors have been constructed by ligation of UDPG-PPase gene into pBI121 for Agrobacterium transformation. The resultant binary vector contains a transcriptional fusion of the UDPG-PPase gene to the CaMV 35S promoter. The identity of the cloned gene cassettes in the pBI series of binary vector was confirmed by DNA sequencing (FIG. 2). The 4-coumarate CoA ligase (4CL) promoter from parsley has been identified as a xylem preferential promoter and the 4CL promoter is highly specific for xylem expression in transgenic tobacco. The 4CL promoter was modified and ligated to the UDPG-PPase gene. The construct was subsequently placed in a binary vector containing the 4CL promoter fused to the UDPG-PPase gene. The details of vector map is showed in FIG. 3.

*E. coli* Expression Vector

An expression vector was constructed to raise antibodies for subsequent analysis of transformed plants. The expression vector was based on the fusion of the UDPG-PPase reading frame to a maltose binding domain (MBP). This pMAL vector provides a method for expression and purifying the UDPG-PPase protein in *E. coli* and is a commercially available vector allowing subsequent purification using a maltose column followed by cleavage to obtain the original UDPG-PPase protein.

Example 2

Tobacco Transformation and Characterization of UDPG-PPase Expression

Transformation

Figure 4:
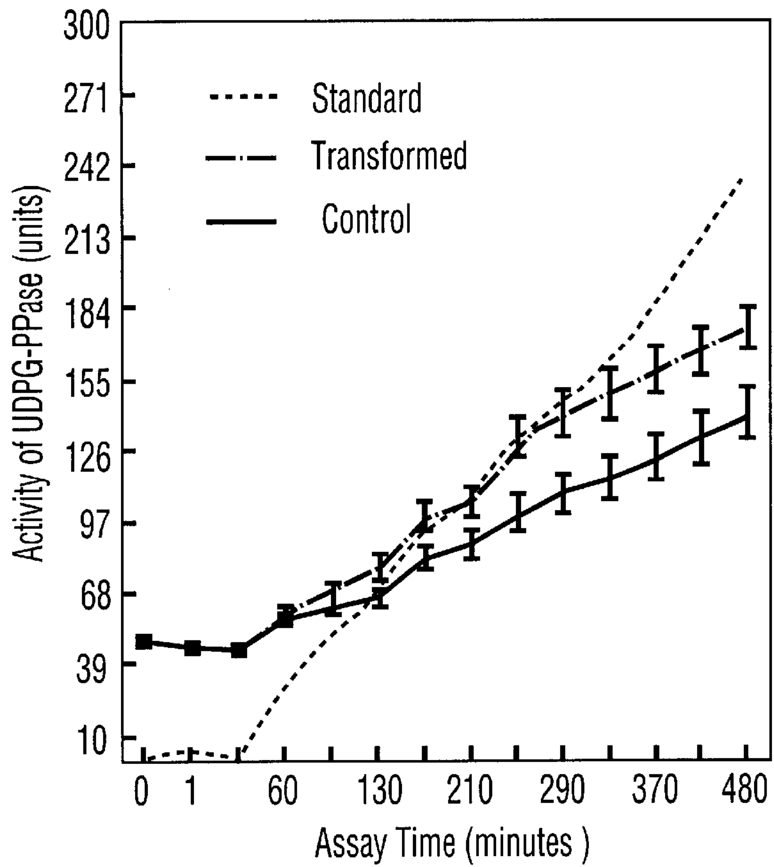
FIG. 4 represents an assay of UDPG-PPase activity in tobacco plants.

The binary vector, pBLAX6 containing the Ax UDPG-PPase gene, was transformed into *A. tumefaciens* strain EHA 105 and this was used to infect *Nicotiana tabacum* c.v. xanthii leaf discs. More than 42 independent $T_0$ transformants were regenerated and individual plants were transferred from tissue culture into a growth room for production of seed. The stable transformation of the UDPG-PPase gene in the $T_0$ tobacco plants was first confirmed by PCR amplification with internal primers (see previous report). Further analyses were carried out by Southern Blot analysis. More than 42 independent transformed plants ($T_0$) have rooted and grown in both sterile MS medium and in soil. Seeds from 24 $T_0$ plants have been harvested and used to generating $T_1$ plants. $T_1$ plants were grown in soil following germination on kanamycin (150 mg/ml). Segregation of kanamycin resistant $T_1$ plants followed expected segregation patterns. The results demonstrated that the UDPG-PPase gene was successfully integrated into the tobacco genome. Activity of the expressed UDPG-PPase gene was assayed in vivo and in vitro by measurement of NADPH formation accompanying the enzyme-coupled conversion to 6-phosphogluconate through G-6-P. In order to test the activity of UDPG-PPase, tobacco leaves from the greenhouse were sampled using a cork borer and ground to a powder with PVPP/sand in liquid nitrogen. The enzyme was extracted with magnesium/glycine-glycine buffer and added into the assay buffer. The formation of NADPH was monitored at 340 nm at 30° C. continuously until a loss of the initial linear reaction rate occurred. The enzyme assay showed that UDPG-PPase activity was significantly higher in transgenic tobacco carrying the UDPG-PPase gene compared to control plants (FIG. 4). Note that in FIG. 4 activity refers to specific activity (units/mg protein). Standard refers to pure commercial enzyme preparation.

TABLE 1

Summary of height growth (cm) of tobacco plants transformed with UDPG-PPase gene versus controls. All plant were regenerated from leaf discs.

| Days of | Control n = 9 | | Transformed n = 42 | | % of |
|---|---|---|---|---|---|
| growth | Avg. | SE | Avg. | SE | control |
| 1 | 9.02 | 0.94 | 9.67 | 0.40 | 107% |
| 20 | 12.25 | 1.16 | 12.54 | 0.43 | 102% |
| 34[a] | 19.60 | 1.55 | 22.61 | 0.54 | 115% |
| 47 | 28.60 | 2.06 | 29.17 | 0.80 | 102% |

[a]Significant at p=0.05

Preliminary data on the height growth of the $T_0$ plants over a six week period is contained in Table 1. During the exponential growth phase the transformed plants were significantly taller than the controls (P=0.05).

Segregation analysis of $T_1$ generation

Seeds from 16 $T_0$ plants were harvested and used for generating the $T_1$ generation. The germination rate of the $T_0$ seeds ranged from 52–93%, averaging 73%. Seeds for the $T_1$ plants were germinated on medium containing 100 or 150 ug/ml kanamycin and segregation of kanamycin resistant seedlings was scored. A Pearson chi-square test showed that most of the transformed tobacco plants contained the inserted genes in a single locus (and presumably in a single copy) due to a segregation ratio of approximately 3 to 1 (Table 2.). Scoring of kanamycin resistance in germinating $T_1$ seedlings was not straight forward. On water-agar, the germination frequency was very low, further, nontransfromed controls and transformed seeds had similar germination frequencies. Conversely with the use of ½ strength MS medium, germination in the presence of kanamycin was high with all seeds, including the controls. Several parameters including root growth, cotyledon color, seedling vigor, seedling size, and the presence of primary leaves were assessed. Currently the only reproducible and reliable method for determination of kanamycin resistance in the seedlings is germination for three weeks on ½ MS containing 150 ug/ml kanamycin and scoring resistance based on the presence or absence of primary leaves.

TABLE 2

Segregation of kanamycin resistant $T_1$ tobacco seedlings based on presence (tolerant) or absence (susceptible) of primary leaves.

| Seeds of $T_0$ lines (ug/mg kanamycin) | Kan resistant | Kan sensitive | Kan+/K |
|---|---|---|---|
| 6.01 (150) | 39 | 13 | 3.0 |
| 6.03 (100) | 35 | 14 | 2.5 |
| 6.05 (100) | 35 | 12 | 2.8 |
| 6.06 (150) | 26 | 15 | 1.7 |
| 6.07 (100) | 35 | 12 | 2.9 |
| 6.08 (150) | 29 | 10 | 2.9 |
| 6.09 (150) | 38 | 12 | 3.2 |
| 6.12 (150) | 35 | 14 | 2.5 |
| 6.13 (150) | 36 | 10 | 3.6 |
| 6 14 (150) | 34 | 12 | 2.8 |
| 6.15 (150) | 29 | 8 | 3.6 |
| 6.23 (150) | 30 | 14 | 2.1 |
| 6.24 (150) | 30 | 18 | 1.7 |
| 6.25 (150) | 34 | 15 | 2.3 |
| 6.33 (150) | 33 | 11 | 3.0 |
| 6.42 (150) | 38 | 12 | 3.2 |
| Control5 | 0 | 44 | 0.0 |
| Control8 | 2 | 46 | 0.0 |

Example 3

Analysis of Protein Expression

Protein Production and Antigen Purification

The protein expression vector pMALAX was used to overproduce the UDPG-PPase-maltose binding protein (MBP) fusion in *E. Coli* after induction with isopropylthiogalactoside (IPTG). A crude protein extract was obtained with guanidine and urea buffers. Purification of the UDPG-PPase-MBP fusion protein was done by affinity chromatography using an amylose resin affinity column, with elution of the purified fusion protein from the column with 10 mM maltose. This purified fusion protein was confirmed to be a pure fraction based on SDS-PAGE and was used for antibody production in rabbits.

Antibody Production

The anti-UDPG-PPase antibody was produced by Enz-Probe Biotechnology, Burnaby, B. C. after immunization of rabbits with the purified UDPG-PPase-MBP fusion protein. A UDPG-PPase specific antibody was prepared from the immunized rabbit serum by affinity purification in the presence of excess maltose binding protein (to displace antibodies which react to this portion of the fused protein). The purified antibody was used to detect the expression of proteins in Western Blotting experiments.

Protein Analysis in Transgenic Tobacco

The protein hybridization was carried out according to Sambrook et al. (1989)[9] with the affinity purified antibody used at a 1:500 dilution. Antibody raised against the purified protein cross-reacted on western blots with the extracted UDPG-PPase protein from both bacteria and transformed plants. Western blots showed that the antibody bound to peptides of 30 KDa and 90 kDa, corresponding to the UDPG-PPase peptide with and without the MBP fusion protein respectively. Removal of the MBP portion of the fusion protein was done by digestion with factor Xa in a modified incubation buffer. Expression of the UDPG-PPase gene in transgenic tobacco plants was inferred by the recognition of the anti-UDPG-PPase antibody to a 30 KDa peptide in the transgenic plants. Antibody binding to a peptide of similar molecular mass has never been detected in non-transformed plants.

Figure 6:
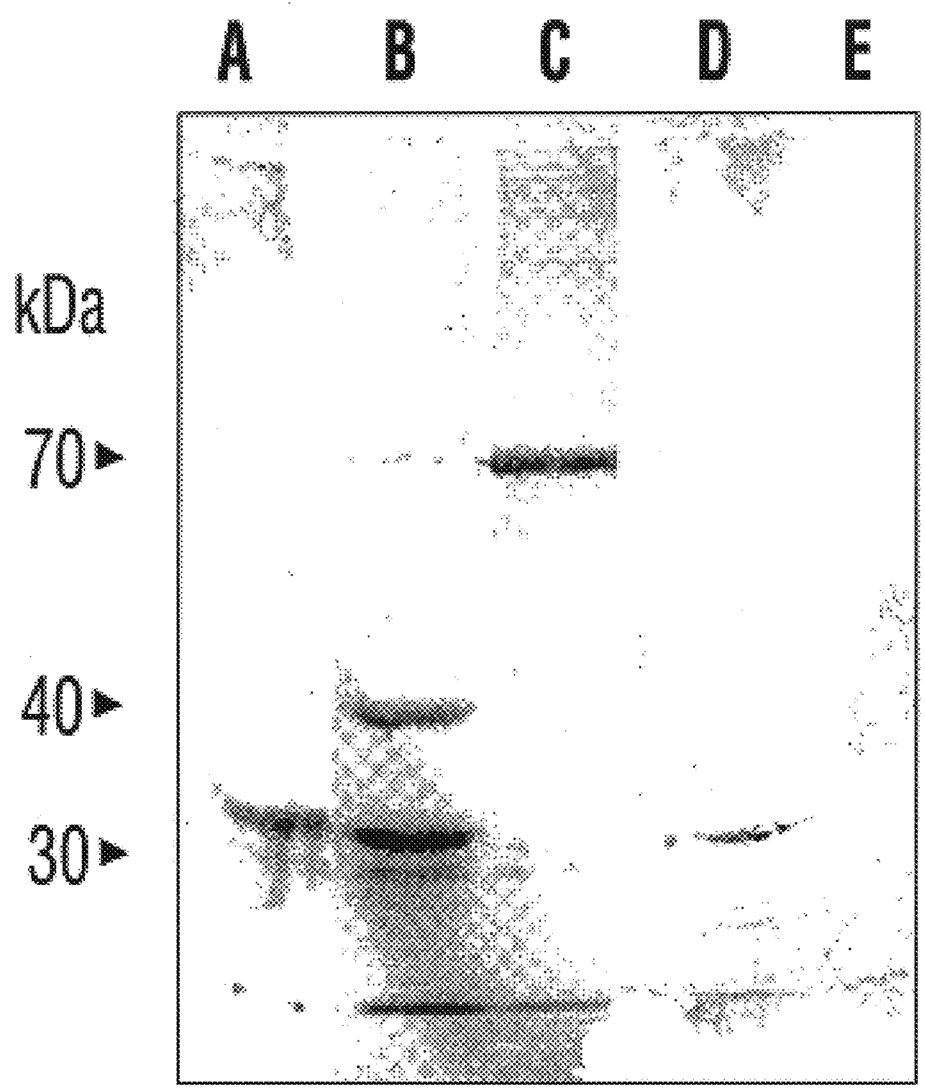
FIG. 6 is a Western Blot analysis of UDPG-PPase protein with the anti-UDPG-PPase antibody.

Although not evident in FIG. 6 (the Western Blot of UDPG-PPase protein with the anti-UDPG-PPase antibody), there is cross-reaction of the anti-UDPG-PPase antibody with several other bands in the protein profile of tobacco. Despite numerous experiments to further purify the antibody and increase the specificity of this antibody, the background still persists. In fact, definitive detection of the UDPG-PPase protein from individual transformed plants has been difficult because of this background. However, cleavage of the fusion protein with factor Xa (as mentioned above) provides a method to obtain higher affinity antibody to UDPG-PPase protein.

Example 4

Cellulose Analysis of Transgenic Tobacco

Cellulose is one of the most important polysaccharides in tobacco and it's production is directly linked to UDPG-PPase. Cellulose analysis of $T_0$ plants were done with both whole plants and stems from mature flowering plants. Approximately 20 g (f.w.) of plant tissue was extracted with azeotropic ethanol-benzene (1:2 w/w) in a Soxhlet apparatus. After extraction, the solution was dried for soluble material analysis. The plant tissue was then ground and thoroughly mixed to make a homogenous sample. One gram of this sample was delignified with sodium chlorite in weak acetic acid and the lignin was washed away by gradual filtration. The entire polysaccharide fraction of the sample was used to determine holocellulose. Removal of hemicellulose was performed by treatment with 24% potassium hydroxide and the pure form of alpha-cellulose was recovered as a white product from filtration through a sintered crucible.

Figure 7:
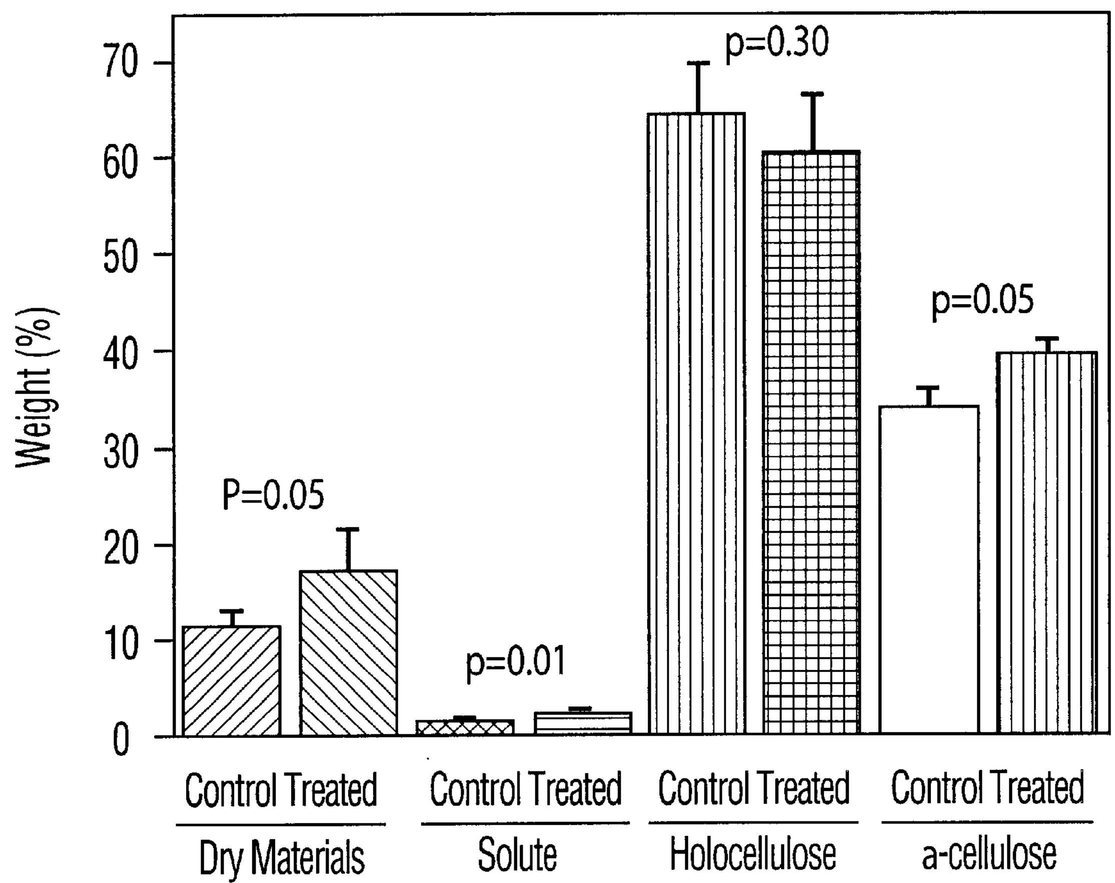
FIG. 7 is a bar graph representing an analysis of cellulose in transformed tobacco plants.

Total biomass and cellulose analysis of five control and five $T_0$ transformed (treated) plants showed that the transgenic plants containing the UDPG-PPase gene had significantly higher dry weight, solute content, and most importantly a-cellulose content (FIG. 7). No significant differences in holocellulose were detected.

Example 5

Protein Expression and Antibody Production

Figure 5:
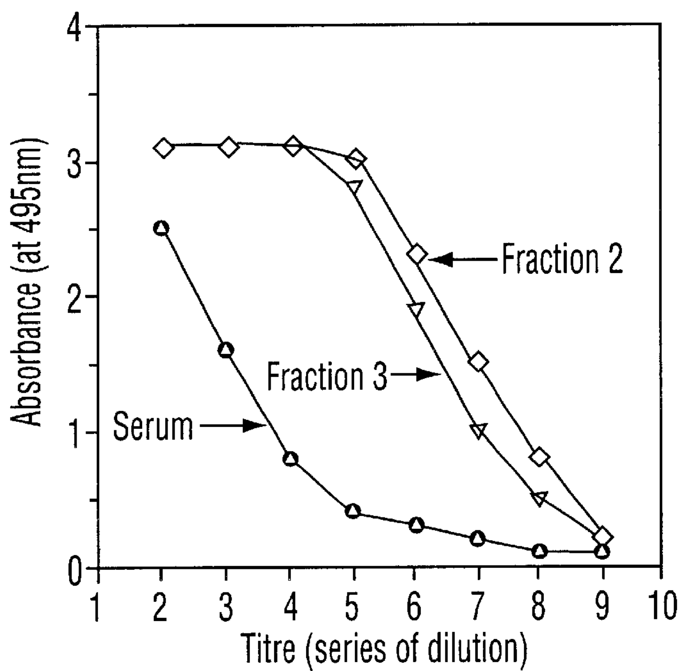
FIG. 5 is a graph representing the titre of anti-UDPG-PPase sera with affinity purification.

The anti-UDPG-PPase rabbit serum was collected from rabbits after immunization with the UDPG-PPase protein produced in *E. coli*. The total antibody was assayed with enzyme-labeled protein. Antibody activity against the purified protein was detected in serum by ELISA at a titre of 32,000; a working ELISA dilution of 1/500 was used. A UDPG-PPase specific antibody, was then prepared by affinity purification in the presence of excess maltose binding domain protein to displace antibodies which react the MBP portion of the fused protein. The titre of anti-UDPG-PPase sera with affinity purification is shown in FIG. 5. Note that Fractions 2 & 3 obtained by elution from an affinity column. The titre dilution is 1/1, 1/500, 1/2000, 1/8000, 1/32000, 1/128000, 1/512000, 1/2048000 contrasted with pre-immune serum (titre series 2 to 9 respectively.) The purified antibody has identified a band on a Western Blot of the same molecular weight as the UDPG-PPase protein.

Example 6

Stable Transformation of Spruce with 4CL-UDPG

Transformation of UDPG-PPase Gene into Spruce

Using biolistics, transformation of spruce somatic embryos with both pBI4CLAX and pUC4CLGUS has been initiated. Over 1,500 interior spruce and 200 Sitka spruce somatic embryos have been bombarded with these constructs. The interior spruce embryos are from four different genotypes, and several different developmental stages. Following particle bombardment, the embryos were allowed to recover two weeks prior to placement on selective medium containing 5 mg/ml kanamycin. Embryos were transferred every three weeks onto fresh kanamycin medium for three transfers and then placed on kanamycin-free medium for an additional three weeks. Embryos were assessed at each transfer for the formation of callus resembling embryogenic callus characterized by clear, glassy, projections consisting of elongated cells subtended with dense head cells resembling a somatic embryo. $T_0$ date, up to 4% of the embryos bombarded with pUC4CLGUS and pBI4CLAX have formed embryogenic callus on kanamycin containing medium.

Histochemical screening with x-gluc to detect GUS activity of embryogenic calli derived from embryos bombarded with the pUC4CLGUS construct has identified 22 interior spruce and one Sitka spruce transformed embryogenic lines. The GUS staining of these lines is surprisingly strong. Over 20 embryogenic lines derived from embryos bombarded with pBI4CLAX grew on kanamycin containing medium.

References Cited

1. Goldchmidt, E. E. and S. C. Huber. 1992. Regulation of Photosynthesis by End-Product Accumulation in Leaves of Plants Stroing Starch, Sucrose and Hexose Sugars. *Plant Physiol.* 99:1443–1448
2. Sonnewald, U. and L. Willmitzer. 1992. Molecular approaches to sink-source interactions. *Plant Physiol.* 99:1267–1270.

3. Shewmaker, C. K. and D. M. Stalker. 1992. Modifying starch biosynthesis with transgenes in potatoes. Plant Physiol. 100:1083–1086.

4. Delmer, D. P. 1987. Cellulose biosynthesis. *Ann. Rev. Plant Physiol.* 38:259–290

5. Delmer, D. P. and Y. Amor. 1995 Cellulose Biosynthesis. Plant Cell 7:987–1000

6. Ross, P., R. Mayer, M. Benziman. 1991. Cellulose biosynthesis and function in bacteria. *Microbiol. Rev.* 55:35–58.

7. Betlach M. R., D. H. Doherty, R. W. Vanderslice. 1987 Process for the synthesis of sugar nucleotides using recombinant DNA methods. International Patent WO 87/05937.

8. Farnum, P., R. Timmis, J. K. Kulp. 1983. Biotechnology of forest yield. *Science* 219:694–702.

9. Sambrook J., E. F. Fritsch and T$_1$ Maniatis. 1989. Molecular Cloning. 2nd Ed. Cold Spring Harbour Laboratory Press: 18. pp. 3–86

We claim:

1. A process of increasing plant growth and/or yield which comprises introducing into a plant a DNA sequence encoding uridine diphosphate-glucose pyrophosphorylase (UDPG-PPase), wherein expression of said sequence modifies the level of cellulose precursors in cells or tissues of the plant and increases plant growth and/or yield.

2. The process of claim 1 wherein the precursor is uridine diphosphate glucose (UDP-glucose).

3. The process of claim 1 wherein the plant is a tree.

4. The process of claim 1 wherein the DNA sequence comprises the UDPG-PPase gene derived from a bacterium.

5. The process of claim 1 wherein the DNA sequence comprises the UDPG-PPase gene derived from *Acetobacter xylinum*.

6. A process of modifying the production of cellulose in a plant which comprises introducing into and expressing in said plant a DNA sequence encoding uridine diphosphate-glucose pyrophosphorylase (UDPG-PPase), wherein expression of said sequence modifies the level of cellulose precursors in cells or tissues of the plant and modifies the production of cellulose in the plant.

7. The process of claim 6 wherein the precursor is UDP-glucose.

8. The process of claim 6 wherein the plant is a tree.

9. A process of modifying the production of cellulose in a plant which comprises introducing into a plant a DNA sequence encoding uridine diphosphate-glucose pyrophosphorylase (UDPG-PPase) flanked by translational start and stop signals and operatively linked to an expression-effecting DNA sequence, wherein expression of said sequence modifies the production of cellulose in cells or tissues of the plant.

10. The process of claim 9 wherein the expression effecting DNA sequence is a promoter directing expression of the UDPG-PPase gene primarily in stem or xylem cells of the plant.

11. The process of claim 9 wherein the expression effecting DNA sequence is a promoter selected from the group consisting of one or more of CaMV 35S and 4CL from parsley.

12. The process of claim 9 wherein the plant is a tree.

13. A plant having modified cellulose producing activity as a result of introducing into said plant or a parent of said plant a DNA encoding uridine diphosphate-glucose pyrophosphorylase (UDPG-PPase), wherein expression of said sequence modifies the level of cellulose precursors in cells or tissues of said plant.

14. The plant of claim 13 wherein the precursor is UDP-glucose.

15. The plant of claim 13 being a tree.

16. The plant of claim 13 wherein the DNA sequence comprises the UDPG-PPase gene derived from a bacterium.

17. A DNA expression vector comprising a DNA sequence encoding a bacterial uridine diphosphate-glucose pyrophosphorylase (UDPO-PPase), flanked by translational start and stop signals and operatively linked to a DNA sequence effecting expression in plants.

18. A genetically modified seed comprising a foreign DNA sequence encoding uridine diphosphate-glucose pyrophosphorylase (UDPG-PPase), wherein expression of said sequence modifies the level of cellulose precursors in cells or tissues of the plant grown from said seed.

* * * * *